United States Patent [19]

Fishbein

[11] Patent Number: 4,621,637

[45] Date of Patent: Nov. 11, 1986

[54] SURGICAL DEVICE FOR REMOVING BONE AND TISSUE FROM JOINT MEMBERS

[76] Inventor: Meyer Fishbein, 12020 Saltair Pl., Los Angeles, Calif. 90049

[21] Appl. No.: 635,753

[22] Filed: Jul. 30, 1984

[51] Int. Cl.[4] .............................................. A61F 17/32
[52] U.S. Cl. .................................. 128/305; 408/227; 128/92 V
[58] Field of Search .................. 128/305, 92 R, 92 E, 128/303 R, 83; 408/227

[56] References Cited

U.S. PATENT DOCUMENTS

| | | | |
|---|---|---|---|
| 3,630,204 | 12/1971 | Fishbein | 128/305 |
| 3,633,583 | 1/1972 | Fishbein | 128/92 E |
| 3,702,611 | 11/1972 | Fishbein | 128/305 |
| 4,023,572 | 5/1977 | Weigand et al. | 128/305 |
| 4,116,200 | 9/1978 | Braun et al. | 128/92 E |
| 4,131,116 | 12/1978 | Hedrick | 128/92 E |
| 4,467,801 | 8/1984 | Whiteside | 128/305 |
| 4,528,980 | 7/1985 | Kenna | 128/92 EB |

Primary Examiner—Gene Mancene
Assistant Examiner—Wenceslao J. Contreras
Attorney, Agent, or Firm—Fulwider, Patton, Rieber, Lee & Utecht

[57] ABSTRACT

This invention is directed to an improved surgical tool to remove tissue or bone from a bone joint member prior to installing a prosthetic device wherein the device basically comprises a cutting head and a rotary device member. The cutting head comprises a support base coupled to the rotary drive, a hollow shell with one or more slots, and one or more cutting or skiving blades projecting through the slots and supported by the support base.

14 Claims, 10 Drawing Figures

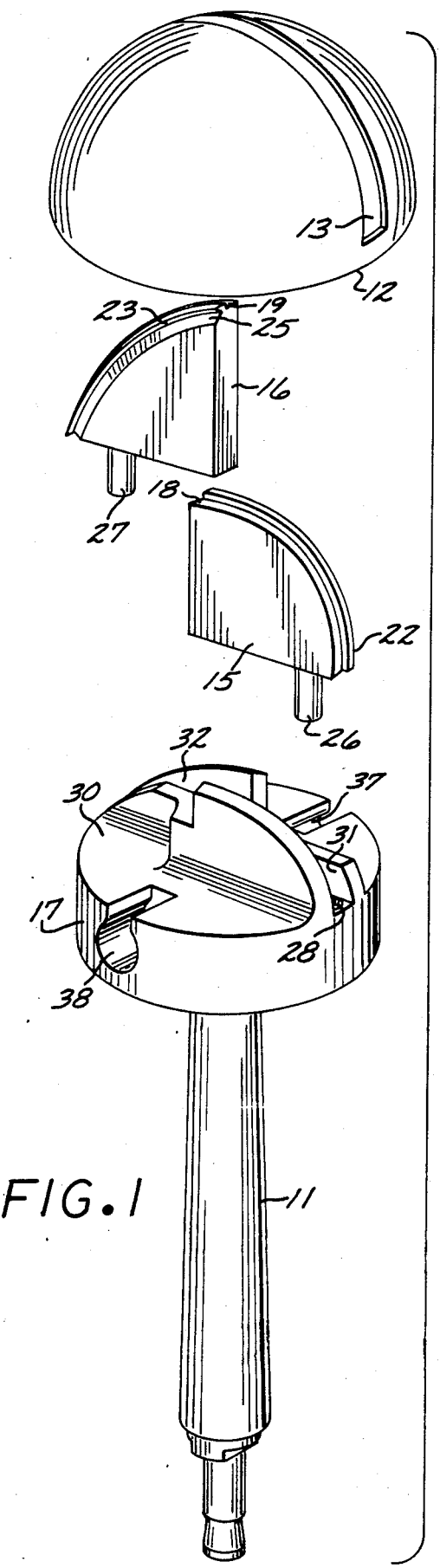
FIG.1
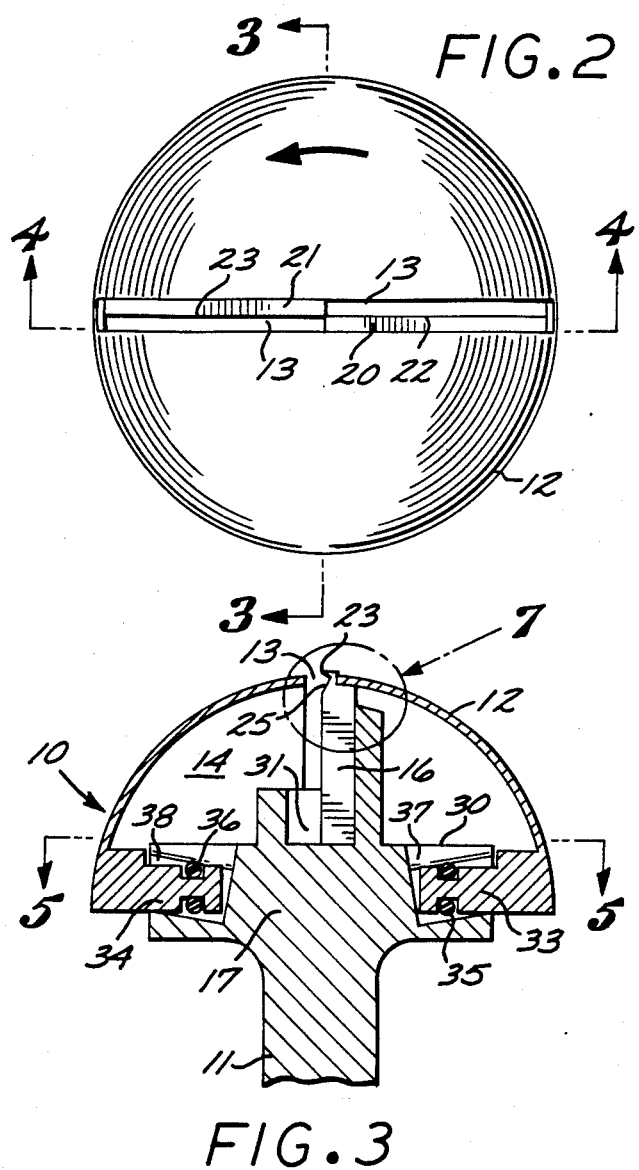
FIG.2
FIG.3
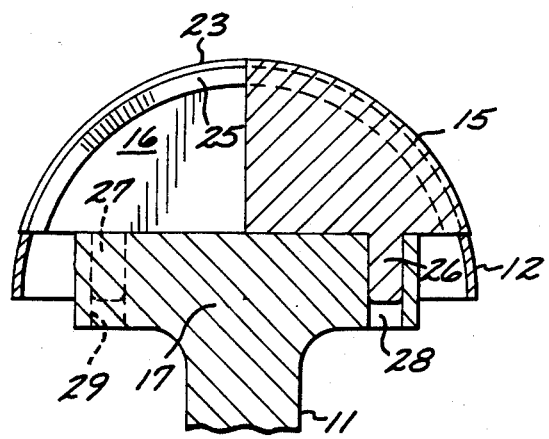
FIG.4

SURGICAL DEVICE FOR REMOVING BONE AND TISSUE FROM JOINT MEMBERS

BACKGROUND OF THE INVENTION

This invention relates to a rotating surgical tool for removing thin layers of articular cartilage and bone from bone members in the preparation of a joint socket to receive a joint prosthesis.

In the treatment of severe cases of arthritis and other degenerative joint diseases, particularly of the hip joint, it is now common practice to shape the hip joint socket and remove the hip joint ball and to thereby be replaced by a total hip prosthesis formed from artificial materials. Prior to installing the artificial hip joint socket, articular cartilage and bone is removed from the socket in the process of reshaping the acetabulum to accurately match the dimensions of the artificial socket.

In the past, numerous types of milling devices and reamers have been employed with various degrees of success. Some of these devices are disclosed in U.S. Pat. No. 3,630,204 (Fishbein), U.S. Pat. No. 4,023,572 (Weigand et al.), U.S. Pat. No. 4,116,200 (Braun et al.) and U.S. Pat. No. 4,131,116 (Hedrick). Although the devices described in these patents represented substantial improvements over the crude devices which preceded them, i.e., rasps, hammers and chisels, the devices described therein cannot provide the accurate reshaped cavities and the smooth cavity lining required by the modern surgical prosthesis. Moreover, many of these prior devices were costly to manufacture and some could not be aseptically cleaned without the inconvenience of disassembling numerous component parts.

Preferably, the cutting edges of the surgical tool should be able to cut through a wide variety of tissue, such as joint cartilage and bone tissue, ranging in density from the porous or cancellous tissue to the hard sclerotic bone. Surgical tools which merely scrape or tear off tissue operate well on hard bone but they tend to be less effective with soft, porous tissue.

The surgical tools with hollow cutting heads are more widely used than other more open designs because with the hollow head devices cuttings and other debris are captured within the interior of the cutting head so they will not interfere with subsequent procedures. However, the hollow cutting heads are usually drawn into their hemispherical shapes and this method cannot form cutting heads with the accuracy frequently needed. Additionally, if the cutting surfaces are formed integrally with the shell such as with teeth or raised edges of slots, the manufacturing thereof becomes very costly. Resharpening of the cutting surfaces of these tools is for the most part impractical, so the entire cutting shell must be discarded when the cutting surfaces dull.

Ideally, a surgical device for shaping a joint socket such as the acetabulum should be simple in design and construction and economical to manufacture. At present, up to about 30 different sized cutting heads must be available with an incremental difference of ½ mm in the cutting radius between the various sized blades. In order to reduce the manufacturing cost of the devices, it is preferred to have as many standard components as possible. Generally, it is preferred to have a standard sized drive mechanism with the cutting heads of different sizes being adapted to fit on the single drive mechanism. The securing mechanism between the cutting heads and the drive mechanism should be as simple as possible to avoid complicated assembly in changing heads. Moreover, not only should the cutting heads of different sizes be readily changed but also cutting heads of different shapes such as frusto-conically shaped cutting heads should also fit on the same drive mechanism. The device of the present invention satisfies these requirements.

SUMMARY OF THE INVENTION

This invention is directed to an improved surgical tool for removing bone and particularly for the reshaping of sockets or tissue such as the acetabulum of the hip joint to facilitate the installation of part or all of an artificial joint.

The surgical device in accordance with the present invention generally comprises a cutting head fixed to the end of a drive shaft which is adapted to rotate the cutting head during the surgical procedure. The cutting head includes a hollow shell with one or more slotted openings in communication with the interior or inner chamber of the shell. One or more elongated cutting blades are supported by a suitable support base in the interior of the shell and are in alignment with the slotted openings. The cutting surfaces of the blades project marginally through the slotted openings a uniform distance from the outer surface of the shell. The cutting blades and the shell are supported on a support base fixed to the proximal end of the drive shaft.

The leading edges of the cutting surfaces of the blades are oriented in the direction of rotation of the device and they extend outwardly a uniform distance from about 0.01 to 0.1 inch, preferably about 0.02 to 0.05 inch from the outer surface of the hollow shell. The final grinding of the cutting surface to provide the sharpness required occurs on the under surface of the blade. Moreover, the blades may be resharpened in the same manner so that the radius of the cutting surface is not changed.

A curved or angular recess is provided under the cutting surfaces of the blade to direct cuttings and other debris into the interior chamber in the shell.

The shell is preferably coupled to the support base by quick connect means, such as one or more snap-lock connections, which greatly simplifies removing the cuttings and debris from the interior of the shell during use in a sterile environment.

The cutting blades are provided with depending posts which closely interfit matching cavities in the upper surface of the support base to position the blades on the surface so they are aligned with and project through the slots in the shell. The bottom portion of the blades interfit elongated channels provided on the top surface of the base. Thus, the blades and the shell of the cutting head are very easily assembled and disassembled by hand without the use of any tools.

The cutting blades as described herein are accurately ground to razor sharpness and are thus capable of removing thin layers of tissue from a socket lining, thereby accurately generating a cavity of the desired shape in the socket of the desired shape. Moreover, essentially all of the cuttings or debris enter the interior of the shell through the slots to leave a socket cavity which is free of impacted bone tissue that might later be a source of ossification.

The above features and advantages of the invention will become more apparent from the following detailed description, when taken in conjunction with the accompanying exemplary drawings.

DESCRIPTION OF THE DRAWINGS

FIG. 1 is an exploded perspective view of a preferred surgical device embodying features of the present invention;

FIG. 2 is a plan view of the surgical device shown in FIG. 1;

FIG. 3 is a cross-sectional view taken along the lines 3—3 shown in FIG. 2;

FIG. 4 is a cross-sectional view taken along the lines 4—4 shown in FIG. 2;

In the drawings all corresponding parts are numbered the same.

DETAILED DESCRIPTION OF A PREFERRED EMBODIMENT

Figure 5:
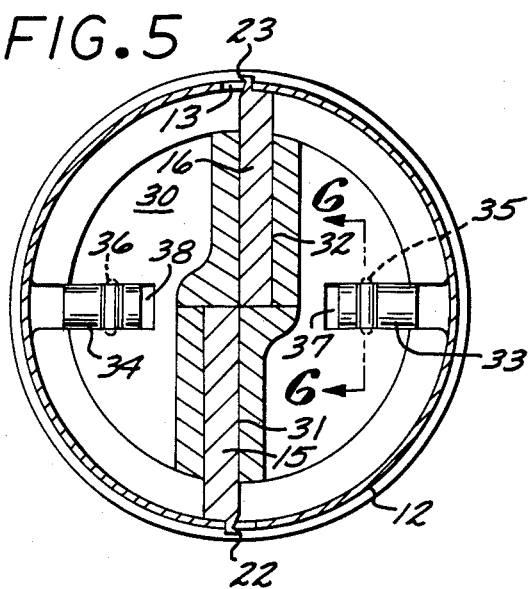
FIG. 5 is a partial cross-sectional view of the top of a cutting blade and the shell utilized in the device shown in FIG. 1.

Illustrated in the accompanying drawings is a surgical device embodying features of the present invention comprising a cutting head 10 and a rotary drive means 11 which can remove tissue or bone from a bone joint member such as a hip socket or femoral head to prepare the joint member for the installation of an artificial lining or covering.

With particular reference to FIGS. 1-5, the cutting head 10 of the surgical device comprises a hollow shell 12 provided with at least one elongated slot 13 which is in communication with the interior or inner chamber 14 thereof. The cutting blades 15 and 16 are generally in alignment with the slots 13 provided in the shell 12 and and are supported on a base member 17 fixed to the drive shaft 11. The blades 15 and 16 are provided with shoulders 18 and 19, respectively, on the upper surfaces thereof which are ground to the same hemispherical radius of the undersurface of the shell 12 in order to support and position the shell 12. The cutting surfaces 20 and 21 of blades 15 and 16 generally have the same shape as the cross section of the shell 12 and project through the slots 13 and beyond the outer surface of the shell 12 by about 0.01 to 0.1 inch, preferably about 0.02 to 0.05 inch. The leading edges 22 and 23 of the cutting surfaces 20 and 21 are oriented in the direction of rotation indicated by the arrow in FIG. 2. Elongated arcuate or angular recesses 24 and 25 are provided in the blades 15 and 16 under the cutting surfaces 20 and 21 to direct cuttings and debris into the inner chamber 14 formed by the interior of shell 12. The top surfaces of the blades 15 and 16 are spherically ground so that, when the under side of the cutting surfaces 22 and 23 are ground to sharpen or resharpen the blades, the cutting radii thereof do not change.

The cutting blades 15 and 16 are provided with depending posts 26 and 27 which tightly fit into the matching cavities 28 and 29 provided in the upper surface 30 of the support base 17. Matching channel guides 31 and 32 are provided in the upper surface 30 of the support base 17 to accurately position blades 15 and 16 in proper alignment with the slots 13 in the shell 12 and to prevent movement thereof during use.

Figure 7:
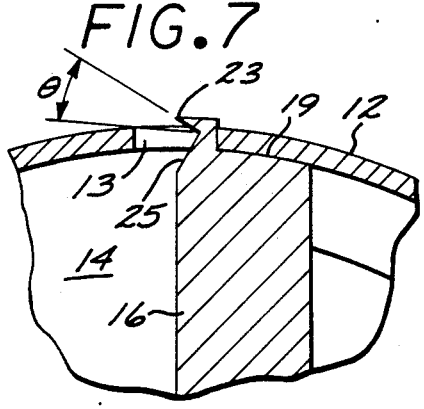
FIG. 7 is an enlarged view of circular area 7 shown in FIG. 3.

The cutting surfaces 20 and 21 are shown in more detail in FIG. 7. The upper longitudinal edge of the blade 15 is generally of the shape of the cross section of the shell 12 and has a arcuate top surface. The underside of cutting surface 22 is at an angle with the outer surface of the shell 12 of less than 90° preferably less than 60°. This requirement ensures that the tissue or bone removal is a cutting or skiving operation as opposed to a scraping action where the tissue or bone is torn or scrapped away from the socket as is common with prior devices. Moreover, it allows the blade to be sharpened without changing the cutting radius of the blade.

Figure 6:
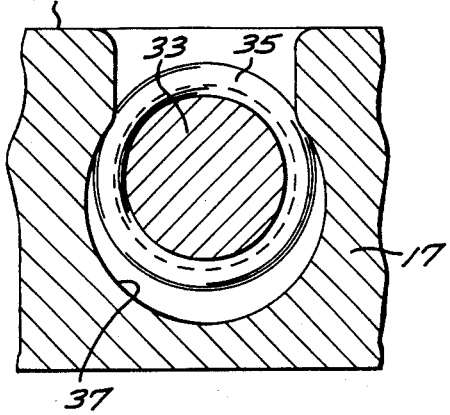
FIG. 6 is a sectional view taken along the lines of 6—6 shown in FIG. 5.

As best shown in FIGS. 3 and 5, the shell 12 is provided with at least two inwardly directed posts 33 and 34 at the lower edge thereof which preferably have resilient elastomeric collars or O-rings 35 and 36 in order to provide a snap-fit connection when pushed into the open channels 37 and 38 in the support base 17 which are narrowed slightly at the top thereof to facilitate the snap-fit connection shown in FIG. 6. Other types of quick connect disconnect means can also be employed.

The support base 17 can be fixed to the end of the drive shaft 11 in any suitable manner or, as shown in the drawings, be made integral therewith.

Figure 8:
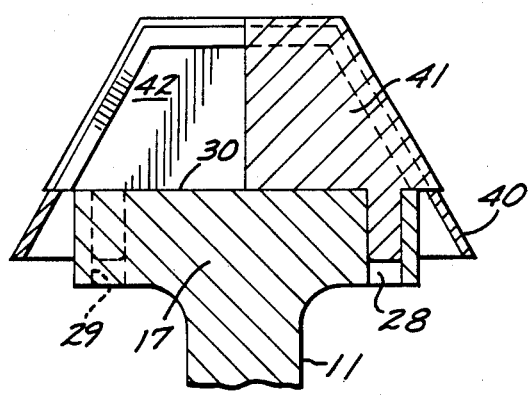
FIG. 8 is a cross sectional view of an embodiment utilized to form a frusto-conical shaped cavity in a bone socket.

In the embodiment shown in FIG. 8, the shell 40 and blades 41 and 42 cut and shape the socket to provide a frusto conical shaped cavity therein. The details of the device are essentially the same as the embodiment shown in FIGS. 1-5 except the shape of the shell 40 and the cutting blades 41 and 42.

Figure 9:
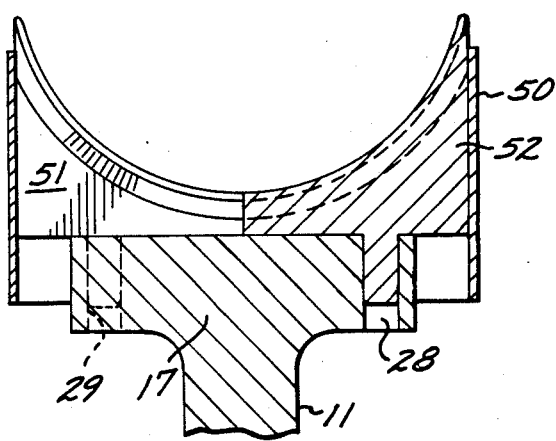
FIG. 9 is a cross-sectional view of another embodiment utilized to remove tissue from the head or condyle of an elongated bone.
Figure 10:
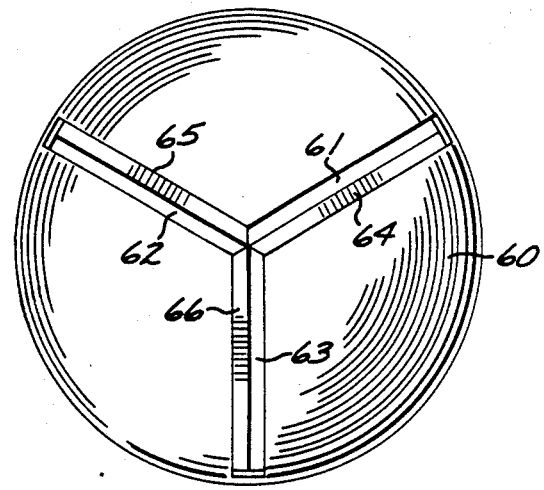
FIG. 10 is a plan view of an embodiment in which the cutting head has a plurality of slots.

FIG. 9 illustrates embodiment for removing bone tissue from the rounded end of a long bone such as the head of the femur. The device is essentially the same as that shown in the other drawings except the outer surface of the shell 50 is concave instead of convex. Moreover, the blades 51 and 52 are essentially the same except that the arcuate shape of the outer edge of the blades 51 and 52 follow the concave outer surface of shell 50.

FIG. 8 is a plan view of an embodiment which illustrates a shell 60 which three elongated equally spaced slots 61, 62 and 63 therein with the cutting surfaces of three blades 64, 65 and 66 projecting through the slots 61, 62 and 63 in a manner previously described.

In the operation of the surgical device of the invention, the cutting head is pushed into a socket and caused to be rotated about its axis so the cutting surfaces of the blades extending outwardly from the shell can remove thin layers of bone or tissue from the lining thereby reshaping the socket to facilitate receiving a prosthesis. When the shell 12 is pushed into the socket, the elastomeric collars 35 and 36 on posts 33 and 34 allow a small amount of movement of the shell 12 toward the support base 17 thereby extending the cutting surfaces 22 and 23 of the blades 15 and 16 further beyond the shell 12 and thereby effecting a deeper cut into the lining of the socket as the device is rotated about its axis. The posts 33 and 34, which are on a line of symmetry, permit a limited degree of blade and shaft motion about this line relative to the shell, which provides a degree of self centering capability.

When it becomes necessary to remove the shell 12, for example, when the cutting head is filled with cuttings and debris, or when the shell 12 must be changed to go to a larger size or different shape, the shell 12 is merely gripped with one hand and, with the drive shaft 11 in the other, the shell 12 is lfited away from the support base 17 to disengage the posts 33 and 34 from the channels 37 and 38. The blades 15 and 16 are similarly removed by lifting them out of the channels 31 and 32 provided in the support base 17.

The shaft, the blades and the shell can be made from conventional materials such as hardened steel or other suitable materials such as aluminum alloys.

The surgical tool of the invention provides a substantial improvement in the accuracy of the reshaped cavity and the smoothness of the resultant cavity lining. The blades, which are relatively inexpensive to manufacture, can be readily machined so the cutting arc of the blade can be maintained to tolerances within ±0.001 inch and usually within ±0.0005 inch which contributes greatly to the accuracy of the reshaped cavity.

Because of the relatively low cost of manufacturing the blades, they can be disposed of after use but, if desired, the used blades can be resharpened. As previously mentioned in a preferred embodiment the blades can be resharpened from the underside of the cutting surfaces so the cutting radius of the blades do not change.

The quick connection of the shell and placement of the blade greatly facilitates changing the size of the cutting head and to clean the cutting head during and after use.

It is obvious that modifications and improvements can be made without departing from the concepts of the invention.

I claim:

1. A rotary surgical device for removing bone or tissue from the socket or the head of a bone joint member to facilitate the installation of a prosthetic device in the socket or on the head of such bone joint member, comprising:
   a. a support base;
   b. means to rotate the support bass about an axis thereof;
   c. a hollow shell detachably secured to the support base having at least one elongated slot therein which is in communication with the interior of the shell and which provides access thereto; and
   d. at least one elongated cutting blade aligned with the elongated slot in the hollow shell having
      i. a lower portion which is supported by the support base in a torque transmitting relationship therewith and to drive the blade about the axis of rotation of the support base
      ii. an upper portion with at least one cutting surface which projects through the elongated slot and extends a short distance beyond the outer surface of the hollow shell, said upper portion having means to guide bone or tissue removed by the cutting surface from the bone joint member through the slot in the shell and into the interior thereof.

2. The surgical device of claim 1 wherein the cutting surfaces of the blades project a uniform distance from the outer surface of the shell from about 0.01 to 0.1 inch.

3. The surgical device of claim 1 wherein the cutting surface of the blade projects a uniform distance from the outer surface of the shell from about 0.02 to 0.05 inch.

4. The surgical device of claim 1 wherein a support base, which is fixed to the proximal end of a drive shaft, supports one or more cutting blades in alignment with the one or more slots in the shell.

5. The surgical device of claim 4 wherein the upper portion of the support base is provided with open channels which position the cutting blades in proper alignment with the slots in the shell.

6. The surgical device of claim 5 wherein the blades are provided with depending posts on the lower portion thereof which tightly interfit matching cavities in the surface of the support base in the bottom of the open channels.

7. The surgical device of claim 1 wherein the cutting blades are provided with elongated recesses under the cutting surfaces thereof to direct cuttings and debris into the interior of the shell.

8. The surgical device of claim 1 wherein the cutting blades are provided with shoulders on the upper surface thereon which are ground to the same hemispherical radius as the undersurface of the shell.

9. The surgical device of claim 1 wherein the shell is at least in part hemispherically shaped and the outer surface thereof is convex.

10. The surgical device of claim 1 wherein the shell is at least in part hemispherically shaped and the outer surface thereof is concave.

11. The surgical device of claim 1 wherein the shell is at least in part frusto-conically shaped.

12. The surgical device of claim 1 wherein the shell is joined to the support base by means of a snap-fit connection.

13. The surgical device of claim 12 wherein the shell is provided with at least two inwardly directed support posts on the interior thereof which are adapted to interfit into open channels provided in the upper surface of the support base having slightly narrowed openings to effect a snap lock connection.

14. The surgical device of claim 13 wherein resilient elastomeric collars or O-rings are provided on the inwardly directed support posts on the shell to facilitate a snap-fit connection in the channels provided in the support base.

* * * * *